United States Patent
Sakata et al.

(10) Patent No.: US 7,938,947 B2
(45) Date of Patent: May 10, 2011

(54) FLOW CONTROL DEVICE, MICROREACTOR AND USE THEREOF

(75) Inventors: Yusaku Sakata, Okayama (JP); Akinori Muto, Okayama (JP); Thallada Bhaskar, Mohkampur (IN)

(73) Assignee: National University Corporation Okayama University, Okayama-Shi, Okayama (JP)

(*) Notice: Subject to any disclaimer, the term of this patent is extended or adjusted under 35 U.S.C. 154(b) by 672 days.

(21) Appl. No.: 11/883,942

(22) PCT Filed: Feb. 17, 2006

(86) PCT No.: PCT/JP2006/302803
§ 371 (c)(1),
(2), (4) Date: Aug. 8, 2007

(87) PCT Pub. No.: WO2006/088120
PCT Pub. Date: Aug. 24, 2006

(65) Prior Publication Data
US 2008/0274038 A1    Nov. 6, 2008

(30) Foreign Application Priority Data
Feb. 21, 2005 (JP) ................. 2005-044660

(51) Int. Cl.
*C02F 1/40* (2006.01)
(52) U.S. Cl. ........ 204/600; 204/660; 204/557; 204/564; 210/222; 210/223; 210/695; 422/129; 422/186.01
(58) Field of Classification Search .......... 423/493, 423/130; 204/600, 660, 557, 564; 422/129, 422/187, 186.01; 137/826, 827; 210/222, 210/223, 695
See application file for complete search history.

(56) References Cited

U.S. PATENT DOCUMENTS

| | | | |
|---|---|---|---|
| 6,095,189 A * | 8/2000 | Ben-Shalom | 137/606 |
| 6,244,738 B1 | 6/2001 | Yasuda et al. | |
| 6,932,951 B1 * | 8/2005 | Losey et al. | 422/211 |
| 7,032,607 B2 * | 4/2006 | Burns | 137/14 |
| 2003/0012657 A1 | 1/2003 | Marr et al. | |

(Continued)

FOREIGN PATENT DOCUMENTS

CA    2189783 A1    11/1995

(Continued)

OTHER PUBLICATIONS

Muto et al., "Y-Pattern Microchannel Reactor with Settler and Extraction Properties of Copper Ion", Kagaku Kogaku Ronbunshu, Mar. 2004, pp. 159-163, vol. 30, No. 2.

(Continued)

*Primary Examiner* — Melvin C Mayes
*Assistant Examiner* — Melissa Stalder
(74) *Attorney, Agent, or Firm* — Buchanan Ingersoll & Rooney PC (57) ABSTRACT

A microreactor containing a plurality of introduction channels 21 and 22 for introducing a plurality of liquids, a merging section 23 for merging the plurality of introduction channels 21 and 22, and a reaction channel 41 located on a downstream side of the merging section 23, characterized in that a flow control section 80 is located on a downstream side of the merging section 23 and an upstream side of the reaction channel 41, and the flow control section 80 contains in a channel 81 thereof a movable particle 82. According to the constitution, such a microreactor can be provided that the flow state in the reaction channel 41 is controlled to realize a flow state with good reproducibility.

20 Claims, 8 Drawing Sheets

U.S. PATENT DOCUMENTS

| | | |
|---|---|---|
| 2004/0155213 A1 | 8/2004 | Yoo |
| 2005/0161099 A1 | 7/2005 | Akema et al. |
| 2006/0292032 A1 | 12/2006 | Hataoka et al. |

FOREIGN PATENT DOCUMENTS

| | | |
|---|---|---|
| EP | 1441132 A2 | 7/2004 |
| EP | 1544287 A1 | 6/2005 |
| JP | 09-512742 A | 12/1997 |
| JP | 11-347392 A | 12/1999 |
| JP | 2004-50401 A | 2/2004 |
| JP | 2004-181298 A | 7/2004 |
| JP | 2004-305938 A | 11/2004 |
| JP | 2004-321063 A | 11/2004 |
| WO | WO 01/64332 A1 | 9/2001 |
| WO | WO 2004/018614 A1 | 3/2004 |
| WO | WO 2006/085443 A1 | 8/2006 |

OTHER PUBLICATIONS

Okamoto, "Micro Hanno Kagaku ni kansuru Jitsuyoka no Doko" (Trends on Practical Application of Microreaction Chemistry), Kagaku Sochi, Sep. 2004, pp. 74-80, vol. 46, No. 9.

Okamoto et al., "New Methods for Increasing Productivity by Using Microreactors of Planar Pumping and Alternating Pumping Types", Chemical Engineering Journal, Nov. 28, 2003, pp. 57-63, vol. 101, No. 1-3.

Extended European Search Report dated Apr. 8, 2010 in European Application No. 06713944.

* cited by examiner

FLOW CONTROL DEVICE, MICROREACTOR AND USE THEREOF

TECHNICAL FIELD

The present invention relates to a flow control device containing a plurality of introduction channels for introducing liquids and a merging section for merging the plurality of introduction channels. It also relates to a microreactor containing a plurality of introduction channels for introducing liquids, a merging section for merging the plurality of introduction channels, and a reaction channel located on a downstream side of the merging section, in which the flow state in the reaction channel can be controlled. It further relates to use of the flow control device and the microreactor.

BACKGROUND ART

In a conventional chemical reaction process, there was a demand of improvement in efficiency by scale-up. In recent years, however, a microreactor, which is a reactor having been scaled down, receives attention owing to such demands as reduction of environmental burdens, resource saving and energy saving. In particular, it becomes a much more real possibility associated with progress of microfabrication technique and microanalysis technique.

It has been known that the following advantages are obtained by reducing a reactor in size. (1) A microreactor has a small reaction space owing to the small dimension thereof. Accordingly, the diffusion distance of molecules is short to facilitate quick molecule migration on mixing, extraction and the like, whereby a period of time required for reaction and extraction can be shortened. (2) Reaction and molecule migration at an interface between liquids or between liquid and solid undergoes efficiently owing to a larger surface area per unit volume. (3) Heat exchange is quickly conducted owing to a small heat capacity of a liquid in the channel, whereby a uniform reaction temperature can be easily maintained, and quick heating and cooling can be easily conducted.

As having been described, a microreactor has such characteristics that are not found in a large reaction device, and is being expected to exert great contribution on synthesis reaction experiments for screening chemical reagents and the like. It is also expected to exert contribution on development of a novel chemical process. In a part of the fields of fine chemicals, it is also expected to produce a product industrially by using a microreactor.

However, associated with reduction in size of the reaction field, such a flow phenomenon is exhibited that is different from those in a conventional macroscopic reaction. For example, in the case where the diameter of the channel is considerably reduced, the Reynolds number is decreased to make a laminar flow dominant. Accordingly, such a flow phenomenon is exhibited that is largely different from those in a turbulent flow caused by mechanical agitation in a macroscopic scale. Furthermore, the surface tension has large influences since the surface area per volume is increased. Consequently, a flow state that is largely different from those in a macroscopic reaction is exhibited, and it therefore is important to control the state certainly.

Various proposals have been made in a microreactor on measures for accelerating mixing of a reaction liquid. For example, Patent Document 1 discloses a method of mixing a plurality of reactants, which are divided into a number of channels respectively, by feeding them to a reaction chamber. Patent Document 2 discloses a method of mixing by agitation with an ultrasonic vibrator. Patent Document 3 discloses that a minute agitator formed of carbon nanotubes is rotated in a concave part of a channel to attain agitation, whereby a laminar flow is changed to a turbulent flow to shorten the reaction time. In the case where these methods are employed, however, it is necessary to make the configuration of the channel complex, or to dispose a vibrator or an agitator for mixing, whereby the device are not necessarily designed easily. Furthermore, in the case where liquids that are incompatible with each other are dispersed too finely, there is such a possibility that it is difficult to separate the liquids again for recovery.

After reacting two kinds of liquids incompatible with each other by mixing in a microreactor, it is preferred that the liquids are again separated and recovered after the reaction in consideration of reuse of the solvent and purification and analysis of a product. Patent Document 4 discloses a method of merging two kinds of reaction liquids introduced from two introduction ports, then conducting an interface reaction while the liquids are in contact with each other in a laminar flow state, and then separating the liquids for recovering from two recovering ports. In this method, the liquids are handled as a two-phase flow, but it is considered that it is not necessarily easy to separate and recover them with good reproducibility. Non-patent Document 1 discloses a method of merging two liquids different in specific gravity, and then separating the two liquids in a settler (pool) for recovery. However, the flow state in the channel greatly influences recovering capability. The flow state is liable to change due to the performance of the pump and flow rate, and thus it is not easy to handle the liquids with good reproducibility.

Non-Patent Documents 2 and 3 disclose a method for reacting two kinds of liquids incompatible with each other by flowing them alternately in a channel. According to the method, an alternating flow can be formed with good reproducibility in a state where a laminar flow is dominant, and the specific interface area between the two kinds of liquids can be relatively large. However, it is necessary to use a special pump capable of feeding minute amounts of liquids alternately, which impairs size reduction and simplification of the device.

Patent Document 1
   JP 9-512742 T
Patent Document 2
   JP 11-347392 A
Patent Document 3
   JP 2004-321063 A
Patent Document 4
   JP 2004-181298 A
Non-Patent Document 1
   Akinori Muto, other 3 persons, "Y-Pattern Microchannel Reactor with Settler and Extraction Properties of Copper Ion", Kagaku Kogaku Ronbunshu, vol. 30, No. 2, pp. 159-163 (March of 2004)
Non-Patent Document 2
   Hideho Okamoto, "Micro Hanno Kagaku ni kansuru Jitsuyoka no Doko (Trends on Practical Application of Microreaction Chemistry)", KagakuSochi, vol. 46, No. 9, pp. 74-80 (September of 2004), published by Kogyo Chosakai Publishing, Inc.
Non-Patent Document 3
   Hideho Okamoto, other 2 persons, "New method for increasing productivity by using microreactors of planar pumping and alternating pumping types", Chemical Engineering Journal, vol. 101, No. 1-3, pp. 57-63 (August of 2004)

DISCLOSURE OF THE INVENTION

Problems to be Solved by the Invention

The invention has been made to solve the aforementioned problems, and an object thereof is to control a flow state with a flow control device having a plurality of introduction channels for introducing liquids and a merging section for merging the plurality of introduction channels, so as to realize a flow state with good reproducibility. Another object of the invention is to provide a microreactor having a plurality of introduction channels for introducing liquids, a merging section for merging the plurality of introduction channels, and a reaction channel located on a downstream side of the merging section, in which a flow state in the reaction channel is controlled to realize a flow state with good reproducibility. Still another object of the invention is to provide a method of chemical reaction and a method of extraction using the flow control device or the microreactor.

Means for Solving the Problems

The aforementioned problems are solved by providing a flow control device characterized by comprising a plurality of introduction channels for introducing liquids, a merging section for merging the plurality of introduction channels, and a flow control section located on a downstream side of the merging section, and the flow control section containing in a channel thereof a movable particle.

It is preferred therein that the introduction channels have a circle equivalent diameter of from 0.01 to 2 mm. It is preferred that the particle is capable of oscillating periodically in the channel of the flow control section, and it is also preferred that the particle has a spherical shape. It is preferred that a lower surface or an upper surface of the channel of the flow control section is curved. It is also preferred that the particle is capable of being forcedly moved by applying a magnetic field or an electric field.

The aforementioned problems are solved by providing a microreactor comprising a plurality of introduction channels for introducing liquids, a merging section for merging the plurality of introduction channels, and a reaction channel located on a downstream side of the merging section, characterized in that a flow control section is located on a downstream side of the merging section and an upstream side of the reaction channel, and the flow control section contains in a channel thereof a movable particle.

It is preferred therein that the reaction channels have a circle equivalent diameter of from 0.01 to 2 mm. It is preferred that the particle is capable of oscillating periodically in the channel of the flow control section, and it is also preferred that the particle has a spherical shape. It is preferred that the channel of the flow control section has a cross sectional area that is larger than a cross sectional area of the reaction channel, and the particle has such a dimension that the particle is capable of moving in the channel of the flow control section but is not capable of entering in the reaction channel.

It is preferred in the microreactor that a lower surface or an upper surface of the channel of the flow control section is curved. It is also preferred that the particle is capable of being forcedly moved by applying a magnetic field or an electric field. It is preferred that the reaction channel is bent periodically, and is also preferred that the reaction channel is bent in the vertical direction. It is preferred that the microreactor further comprises a separating section having a larger cross sectional area on a downstream side of the reaction channel, and the separating section has an upper part and a lower part connected to channels for deriving the liquids after separating.

The aforementioned problems are solved by providing a method of chemical reaction using the microreactor, characterized in that a plurality of liquids that are incompatible with each other are introduced to the plurality of introduction channels, and chemical reaction proceeds in the reaction channel. It is preferred therein that the chemical reaction proceeds in the reaction channel forming therein an alternating flow. It is also preferred that the alternating flow is formed by periodical oscillation of the particle. It is preferred that the microreactor further comprises a separating section having a larger cross sectional area on a downstream side of the reaction channel, the separating section has an upper part and a lower part connected to channels for deriving the liquids after separating, a liquid having a low density is derived from the channel of the upper part, and a liquid having a high density is derived from the channel of the lower part.

The aforementioned problems are solved by providing a method of extraction using the microreactor, characterized in that a plurality of liquids that are incompatible with each other are introduced to the plurality of introduction channels, and extraction proceeds in the reaction channel. It is preferred therein that the extraction proceeds in the reaction channel forming therein an alternating flow.

ADVANTAGE OF THE INVENTION

According to the invention, a flow state is controlled with a flow control device having a plurality of introduction channels for introducing liquids and a merging section for merging the plurality of introduction channels, so as to realize a flow state with good reproducibility. In addition, in a microreactor having a plurality of introduction channels for introducing liquids, a merging section for merging the plurality of introduction channels, and a reaction channel located on a downstream side of the merging section, a flow state in the reaction channel is controlled in a simple manner to realize a flow state with good reproducibility.

BRIEF DESCRIPTION OF THE DRAWINGS

[FIG. 1]
[FIG. 2]
[FIG. 3]
[FIG. 4]
[FIG. 5]
[FIG. 6]
[FIG. 7]
[FIG. 8]
[FIG. 9]
[FIG. 10]
[FIG. 11]
[FIG. 12]

[FIG. 13]

[FIG. 14]

[FIG. 15]

[FIG. 16]

DESCRIPTION OF REFERENCE NUMERALS AND SIGNS 10 base plate
11, 12 introduction port
13, 14 deriving port
20 merging plate
23 merging section
30, 50 connecting plate
40 reaction plate
41 reaction channel
60 separating plate
61 separating section
70 backside plate
80 flow control section
82 particle

BEST MODE FOR CARRYING OUT THE INVENTION

Figure 1:
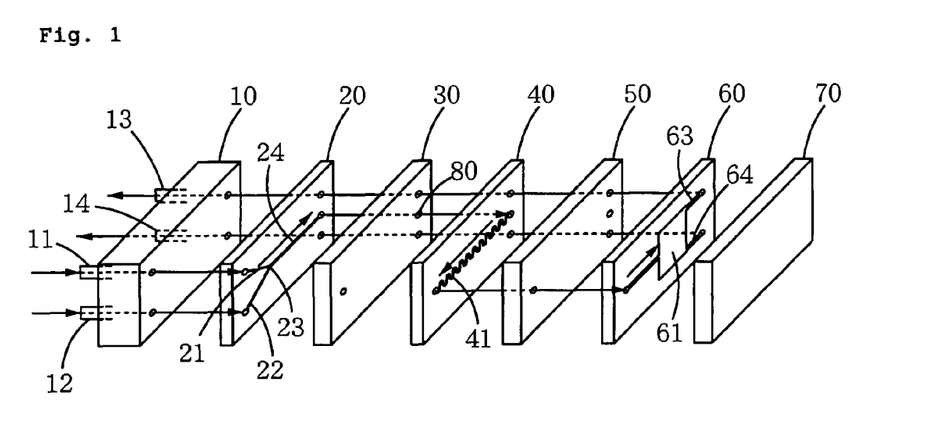
FIG. 1 is an exploded perspective view showing an overview of a microreactor used in an example.
Figure 2:
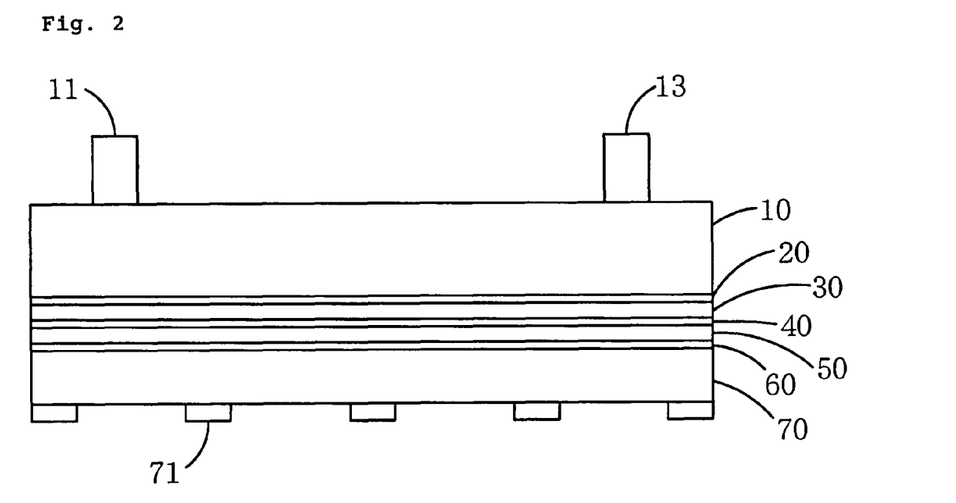
FIG. 2 is a schematic view of the screwed microreactor of FIG. 1 viewed from above.

FIG. 1 is an exploded perspective view showing an overview of a microreactor used in an example of the invention. In this example, seven plate components are superimposed on each other with no space between them, which are used after screwing entirely. The plate components are constituted by a base plate 10, a merging plate 20, a connecting plate 30, a reaction plate 40, a connecting plate 50, a separating plate 60 and a backside plate 70. The arrows in FIG. 1 indicate flows of liquids. In FIG. 1, indication of screws and screw holes is omitted. FIG. 2 is a schematic view of the screwed microreactor viewed from above. The seven plate components are fixed by using 12 screws 71 from the side of the backside plate 70.

The invention will be described below with reference to the figures. In the following description, a microreactor is described as an example, but the invention is not limited to a microreactor. That is, the constitution on a downstream side of the flow control section is not particularly limited, and a reaction channel may not be provided. The texts describing a microreactor as an example in the following description are also for describing the constitution of the flow control section.

The microreactor of the invention has a plurality of introduction channels 21 and 22 for introducing liquids, a merging section 23 for merging the plurality of introduction channels 21 and 22, and a reaction channel 41 located on a downstream side of the merging section 23. In the example shown in FIG. 1, a liquid introduced from an introduction port is introduced to the merging section 23 through the introduction channel 21, and a liquid introduced from an introduction port 12 is introduced to the merging section 23 through the introduction channel 22. The two kinds of liquids are merged in the merging section 23 and flow in a channel 24. While two kinds of liquids are merged herein, three or more kinds of liquids may be merged. In this case, the liquids may be merged at a time in one merging section 23, and may be merged stepwise in a plurality of merging sections.

The introduction channel 21 is not particularly limited in dimension thereof, and in order to obtain a stable flow in a region where a laminar flow is dominant, it is preferably 2 mm or less, more preferably 1.5 mm or less, and further preferably 1 mm or less, in terms of circle equivalent diameter. In order to prevent the pressure for introducing the liquid to the channel from being increased, and to separate and recover the liquid easily, the dimension of the channel is preferably 0.01 mm or more, more preferably 0.05 mm or more, and further preferably 0.2 mm or more, in terms of circle equivalent diameter. The circle equivalent diameter referred herein is a diameter of a circle having the same area as the cross sectional area of the introduction channel 21.

The liquids to be introduced are not particularly limited, and it is preferred in the invention that a plurality of liquids that are incompatible with each other are introduced. In this case, an interface formed between the liquids can be controlled in the channel, and great significance is obtained by employing the microreactor of the invention. The flow ratio upon feeding two kinds of liquids is not particularly limited, and in order to stabilize the flow state, it is preferably from 1/9 to 9/1, and more preferably from 2/8 to 8/2. In the case where the liquids to be introduced are different in density, it is preferred in the microreactor shown in FIG. 1, for example, that a liquid having a low density is introduced from the upper introduction port 11, and a liquid having a high density is introduced from the lower introduction port 12. According to the configuration, the flow state in the merging section 23 is stabilized to facilitate formation of a stable parallel two-phase flow in the channel 24.

Figure 3:
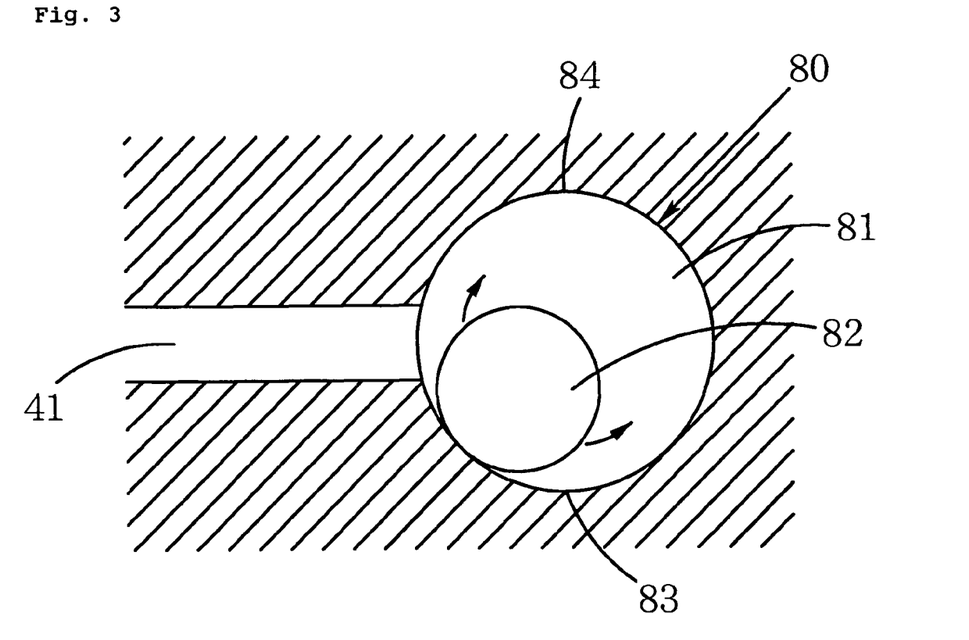
FIG. 3 is a schematic view of a flow control section viewed from side.
Figure 4:
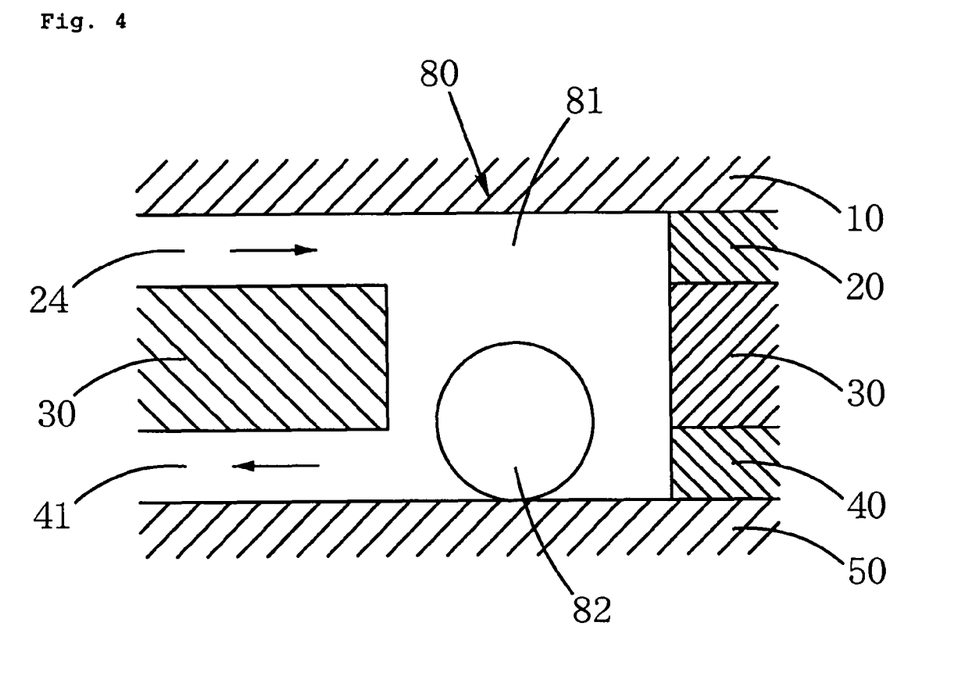
FIG. 4 is a schematic view of a flow control section viewed from above.

In the microreactor of the invention, a flow control section 80 is located on a downstream side of the merging section 23 and an upstream side of the reaction channel 41. In the example shown in FIG. 1, a schematic view of the flow control section 80 viewed from side is shown in FIG. 3, and a schematic view thereof viewed from above is shown in FIG. 4. The flow control section 80 is constituted by a cylindrical channel 81 formed penetrating through the merging plate 20, the connecting plate 30 and the reaction plate 40, and a particle 82 contained therein. The liquid flows from the channel 24 to the reaction channel 41 through the channel 81. The particle 82 is movable within the channel 81, whereby the flow state in the reaction channel 41 on a downstream side of the flow control section 80 is controlled.

Figure 5:
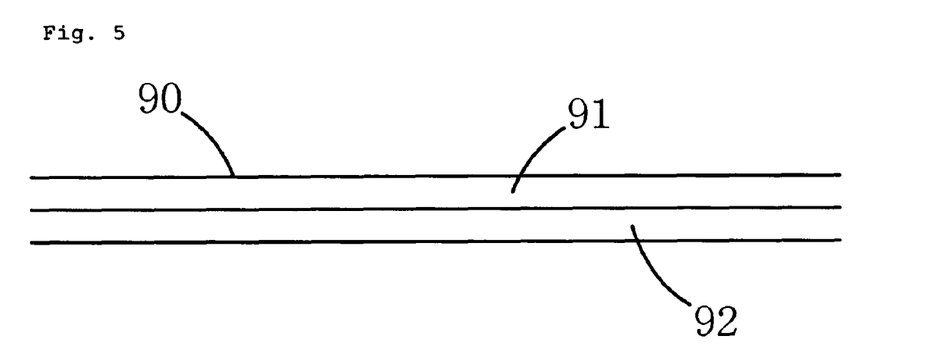
FIG. 5 is a schematic view of a state where a parallel two-phase flow is formed.
Figure 6:
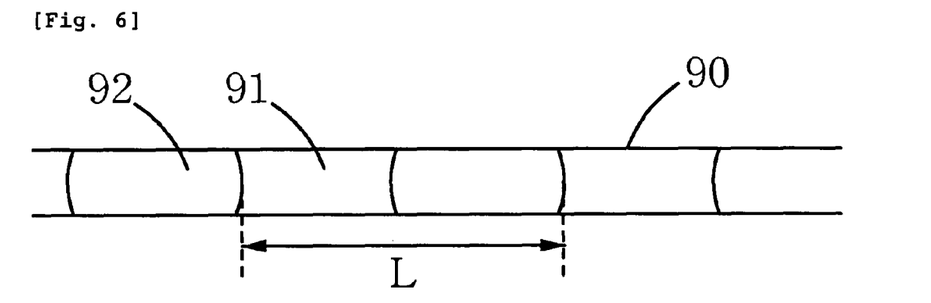
FIG. 6 is a schematic view of a state where an alternating flow is formed.

In the microreactor of the invention, the flow state in the reaction channel 41 is controlled, and the flow state is not particularly limited. In the reaction channel 41, a parallel two-phase flow may be formed, and an alternating flow may be formed. The state formed varies depending on the dimension, shape and direction of the channel, and the amount ratio of provided liquids, flow rates and the like of the liquids to be fed. FIG. 5 shows a schematic view of a state where a parallel two-phase flow containing an oily phase 91 and an aqueous phase 92 is formed in a channel 90, and FIG. 6 shows a schematic view of a state where an alternating flow containing them is formed therein.

In the case where a parallel two-phase flow is formed, good separation property is obtained upon separating and recovering, and the subsequent steps for purification and analysis are simplified. As shown by an example described later, a parallel two-phase flow is formed with good reproducibility through the presence of the flow control section 80, depending on the shape of the reaction channel 41, the flow rate and the like. While the movement of the particle 82 in this case is not completely clear, it is considered that the particle is moved to a position suitable for maintaining the steady flow state, and stays at the position.

As shown by an example described later, in the case where an alternating flow is formed, the extraction rate can be increased as compared to the case where a parallel two-phase flow is formed. It is unexpected that an extraction rate larger than the case of a parallel two-phase flow is obtained even in the case where the pitch of the alternating flow is far larger than the diameter of the channel, in consideration of the distance of molecule migration to the contact interface. It is considered that a special flow state that is advantageous for molecule migration is exhibited in an alternating flow in a minute channel, in which a laminar flow is dominant with a small Reynolds number. For example, it is expected that a circulating flow is generated in each of the phases to provide an effect similar to agitation, and as a result, such a phenomenon occurs that the thickness of the laminar film in the vicinity of the interface is decreased to increase the molecule migration velocity at the interface.

In the case where an alternating flow is formed, liquid droplets having relatively a uniform dimension can be obtained, and therefore, the liquid is easily separated and recovered upon separating and recovering after reaction or extraction. Furthermore, the dimension of the liquid droplets can be easily controlled as compared to the case using a physical method, such as ultrasonic vibration, and the case using a complexly branched channel, and therefore, the reaction rate or extraction rate is difficult to change with the lapse of time to facilitate to provide data with good reproducibility. This is important particularly on operating continuously.

The pitch of the alternating flow formed may not necessarily be uniform, and an alternating flow having a substantially uniform pitch is preferred since good reproducibility is obtained for reaction or extraction. A suitable length of the pitch varies depending on the cross sectional area of the channel, the kind of reaction and the like. The pitch is preferably 0.01 mm or more, more preferably 0.05 mm or more, and further preferably 0.2 mm or more, from the standpoint of the separating and recovering property after reaction or extraction. From the standpoint of the rate of reaction or extraction, the pitch is preferably 30 mm or less, more preferably 20 mm or less, and further preferably 10 mm or less. The pitch referred herein is the distance between an anterior end of a droplet and an anterior end of a subsequent droplet of the same liquid, and is represented by L in FIG. 6.

The particle 82 in the channel 81 of the flow control section 80 preferably has such a shape that facilitates movement thereof in any case where a parallel two-phase flow is formed or an alternating flow is formed. A shape capable of rotating, such as a spherical shape, a spheroid shape and a cylindrical shape, is preferably employed, and a spherical shape is most preferred. The dimension thereof is not particularly limited and is preferably such a dimension that the cross sectional area of the channel 81 is larger than the cross sectional area of the reaction channel 41 and the particle 82 does not enter in the reaction channel 41 while it can move within the channel 81. According to the configuration, the particle 82 can move within the channel 81 of the flow control section 80 without flowing into the reaction channel 41. A narrow part may be provided at the entrance of the reaction channel 41 to prevent the particle 82 from flowing into the reaction channel 41.

The dimension of the reaction channel 41 is not particularly limited and is preferably 2 mm or less, more preferably 1.5 mm or less, and further preferably 1 mm or less, in terms of circle equivalent diameter, in order to obtain a stable flow in a region where a laminar flow is dominant. In order to prevent the pressure for introducing the liquid to the channel from being increased, and to separate and recover the liquid easily, the dimension of the channel is preferably 0.01 mm or more, more preferably 0.05 mm or more, and further preferably 0.2 mm or more, in terms of circle equivalent diameter. The circle equivalent diameter referred herein is a diameter of a circle having the same area as the cross sectional area of the reaction channel 41.

The sphere equivalent diameter of the particle 82 is preferably 0.5 time or more, more preferably 1 time or more, and further preferably 1.7 times or more, the circle equivalent diameter of the reaction channel 41. By using such a particle 82, the effect of masking the flow by the particle 82 is sufficiently exhibited to facilitate control of the flow state. The sphere equivalent diameter of the particle 82 is preferably 5 times or less, more preferably 3 times or less, and further preferably 2.5 times or less, the circle equivalent diameter of the reaction channel 41. The sphere equivalent diameter referred herein is a diameter of a sphere having the same volume as the volume of the particle 82. Specifically, the sphere equivalent diameter of the particle 82 is preferably from 0.01 to 10 mm. The sphere equivalent diameter of the particle 82 is more preferably 0.05 mm or more, and further preferably 0.1 mm or more. The sphere equivalent diameter of the particle 82 is more preferably 5 mm or less, and further preferably 2 mm or less. The number of the particle 82 is not particularly limited and is preferably one.

In the case where a regular alternating flow is to be generated, it is preferred that the particle 81 can oscillates periodically. In order to attain the periodic oscillation, the lower surface 83 or the upper surface 84 of the channel 81 of the flow control section 80 is preferably curved. In the example shown in FIG. 3, the lower surface 83 and the upper surface 84 of the channel 81 are curved, and the particle 82 is on the lower surface 83. When the density of the particle is larger than the density of the flowing liquid, the particle 82 is on the lower surface 83 but is dragged toward the reaction channel 41 with the flow of the liquid flowing from the channel 81 into the reaction channel 41. In the case where two kinds of liquids different in density or polarity flow, it is considered that the position of the particle 82 when one of the liquids mainly flows into the reaction channel is different from the position of the particle 82 when the other of the liquids mainly flows into the reaction channel 41, and as a result, oscillation of the particle 82 is exhibited corresponding to the pitch of the alternating flow formed. When the density of the particle 82 is smaller than the density of the flowing liquid, on the other hand, the particle is in contact with the under side of the upper surface 84 and oscillates while being in contact with the upper surface 84.

In order to form effectively a regular alternating current through oscillation, it is preferred to dispose the particle 82 at a position near the reaction channel 41 rather than the channel 24 in the channel 81 of the flow control section 80, as shown in FIG. 4. For disposing on the side of the reaction channel 41, a method of providing a gradient or a groove in the channel 81 may be employed. Even though the method is not employed, it is sufficient that the liquid is made to flow after disposing the particle 82 on the side of the reaction channel 41 by aspirating or inclining in advance. There are some cases where the particle 82 moves to the vicinity of the entrance of the reaction channel 41 along with the flow without any operation.

In order to obtain a long channel length within a microreactor having a prescribed dimension, the reaction channel 41 is preferably bent. In particular, for effectively forming a regular alternating flow through oscillation, the reaction channel 41 is preferably bent periodically. In this case, a regular alternating flow having the same pitch as the pitch of periodic bending of the reaction channel 41 is liable to form in a manner like resonance with the periodic bending. For generating an alternating flow, it is preferred that the reaction channel 41 is bent in the vertical direction. It is considered that generation of an alternating flow is induced with a plurality of liquids different in density flowing upward and downward within the reaction channel 41. It is particularly preferred for forming effectively a regular alternating flow that the reaction channel 41 is bent periodically in the vertical direction.

The particle 82 may be forcedly moved by applying a magnetic field or an electric field. According to the operation, a regular alternating flow can be easily obtained. For example, by using a particle 82 formed of a material that is attracted to a magnet, the particle 82 can be moved by changing the intensity or direction of the magnetic field. In particular, the particle 82 can be moved in the flow control section 80 by switching repeatedly electromagnets disposed on both sides thereof. A magnetic field can be applied externally to the whole of a number of microreactors disposed in parallel, whereby the constitution of the device can be prevented from being complicated. In the case where a particle 82 that carries electric charge is used, the particle 82 can be moved by applying an electric field. In consideration of the mass and the charge amount of the particle 82, this is often useful when the particle 82 is small in dimension.

The material for the channels is not particularly limited, and glass, ceramics, metals, plastics and the like may be used, which are selected in consideration of workability, chemical resistance, affinity to the liquid and the like. The material for the particle 82 is also not particularly limited, and glass, ceramics, metals, plastics and the like may be used. They are selected in consideration of specific gravity, chemical resistance, affinity to the liquid and the like. A hollow particle may also be used for decreasing the specific gravity. A particle having been subjected to a surface treatment or having a coating on the surface thereof may also be used for adjusting the chemical resistance and the affinity to the liquid. In the case where a liquid is fluidized within a minute channel as in the invention, the surface tension has great influence, and therefore, it is considered that the affinity between each of the plurality of liquids and the materials has importance.

In a preferred embodiment of the microreactor of the invention, a separating section 61 having a larger cross sectional area is provided on a downstream side of the reaction channel 41, and channels 63 and 64 for deriving the liquids after separation are connected to the upper part and the lower part of the separating section 61, respectively. According to the constitution, the liquid passing through the reaction channel 41 is separated upward and downward in the separating section 61, a liquid having a low density is derived from the channel 63 of the upper part, and a liquid having a high density is derived from the channel 64 of the lower part. Thus, the operation for separating the liquid can be carried out inside one microreactor, so as to facilitate the subsequent steps for purification and analysis.

It is sufficient that the cross sectional area of the separating section 61 is larger than that of the reaction channel, and it is preferably 5 times or more, more preferably 10 times or more, and further preferably 20 times or more. In order to prevent the liquid amount from being increased to reduce the dimension of the microreactor, the cross sectional area of the separating section 61 is preferably 500 times or less, more preferably 200 times or less, and further preferably 100 times or less, that of the reaction channel. In view of the separation capability, the cross section of the separating section 61 preferably has a height that is larger than the width, and the height is preferably 2 times or more, more preferably 5 times or more, and further preferably 10 times or more, the width. In general, the height is 500 times or less the width. The separation capability is liable to be improved by increasing the volume of the separating section 61 since the period of time where the liquid is retained in the separating section 61. Therefore, the volume of the separating section 61 preferably occupies from 10 to 90% of the entire volume of from the merging section 23 to the separating section 61. In the case where the occupied proportion of the volume of the separating section 61 is too small, there is a possibility of deteriorating the separation capability, and thus it is more preferably 20% or more, and further preferably 40% or more. In the case where the occupied proportion of the volume of the separating section 61 is too large, the necessary liquid amount is increased, and the device is increased in dimension. Thus, it is preferably 80% or less.

As having been described, the microreactor of the invention is preferably used for attaining chemical reaction or extraction efficiently with good reproducibility by using a plurality of liquids incompatible with each other in a reaction channel 41. For example, a reagent contained in one liquid can be diffused to the other liquid to attain chemical reaction, and a product produced by chemical reaction can be extracted and separated from reagents. Chemical reaction can be attained at an interface between a plurality of liquids. Furthermore, liquids after the reaction or extraction can be easily separated to each other and recovered, whereby for example, such a process can be practiced that a catalyst is recovered, and a solution having the catalyst dissolved therein is used as it is for reaction again. Moreover, it can be used for a pure extraction operation associated with no chemical reaction, such as the case where a hydrophilic compound contained in an oily phase is extracted to an aqueous phase, and the case where a hydrophobic compound contained in an aqueous phase is extracted to an oily phase. In these cases, no chemical reaction proceeds in the reaction channel 41 referred in the invention, but only extraction proceeds, and the invention encompasses embodiments of these kinds.

The microreactor of the invention is particularly preferably applied to a synthesis reaction test for screening chemical reagents since chemical reaction can proceed with small amounts of reagents by using no complicated device. Furthermore, since a stable flow state can be easily provided, data can be obtained with good reproducibility, and it is expected to be useful for setting conditions in various kinds of chemical processes including reaction and extraction. Moreover, in a part of the fields of fine chemicals, such as pharmaceuticals, colorants and electronic materials, a product can be industrially produced by using the microreactor of the invention.

EXAMPLE

The invention will be described below with reference to examples. The specification of the microreactor used in the examples and chemical reaction carried out will be described first.

A test was carried out by using a microreactor having the constitution shown in FIG. 1. The plate components are constituted by a base plate 10, a merging plate 20, a connecting plate 30, a reaction plate 40, a connecting plate 50, a separating plate 60 and a backside plate 70, each of which are described with reference to FIGS. 7 to 15. FIGS. 7 to 15 are all such figures that show the plate components viewed from the right side in FIG. 1. On the peripheries of the plate components, 12 in total of through holes are formed (which are not shown in the figure), and the seven plate components are superimposed on each other with no space between them and entirely screwed for using in the state shown in FIG. 2.

Figure 7:
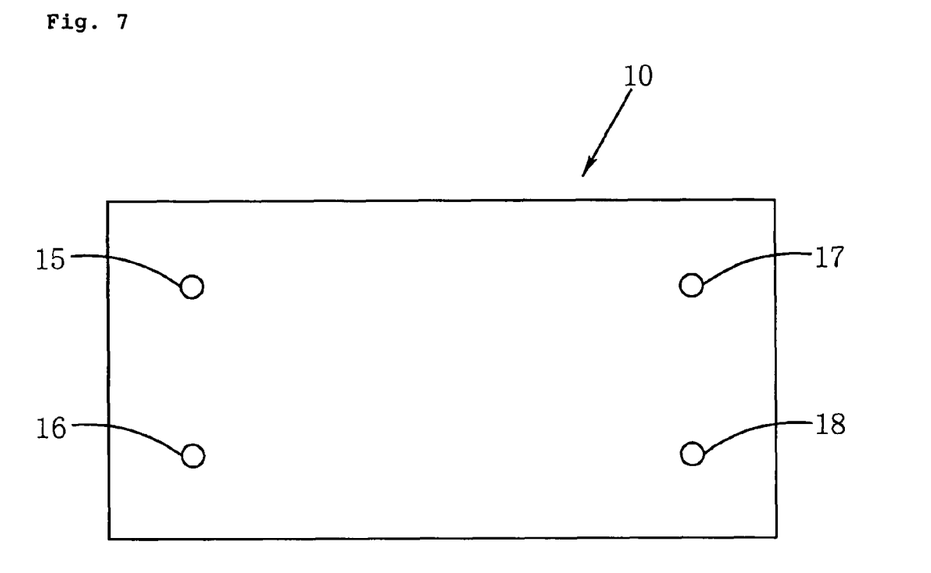
FIG. 7 is a view showing a shape of a base plate.

The base plate 10 is constituted by a stainless steel plate having a length of 60 mm, a width of 30 mm and a thickness of 10 mm, and has the shape shown in FIG. 7. Two introduction ports 11 and 12 and two deriving ports 13 and 14 are provided, and through holes 15, 16, 17 and 18 having a diameter of 2 mm connected to each of them are provided.

Figure 8:
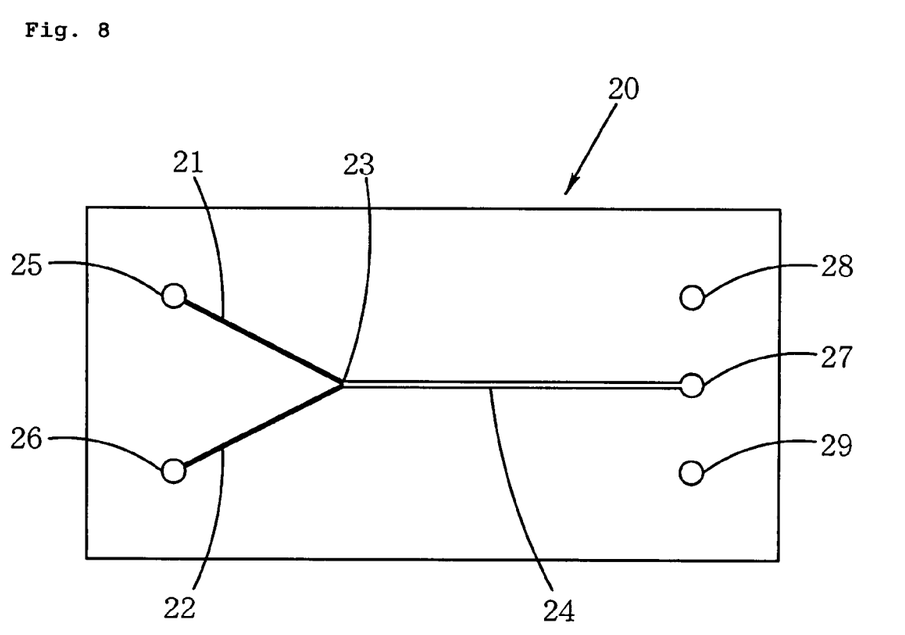
FIG. 8 is a view showing a shape of a merging plate.

The merging plate 20 is a stainless steel plate having a length of 60 mm, a width of 30 mm and a thickness of 0.5 mm and having an Y-shaped slit formed therein, and has the shape shown in FIG. 8. Introduction channels 21 and 22 have a width of 0.25 mm, and a channel 24 on the downstream side of the merging section 23 has a width of 0.5 mm. Through holes 25 and 26 having a diameter of 2 mm are provided at an end part on the upstream side, and are connected to the introduction ports 11 and 12. A through hole 27 having a diameter of 2 mm is provided at an end part on the downstream side, and is connected to a through hole 31 of the connecting plate 30 to constitute a part of a flow control section 80. Through holes 28 and 29 are provided for the liquid having been separated with the separating plate 60 flowing to the deriving ports 13 and 14.

Figure 9:
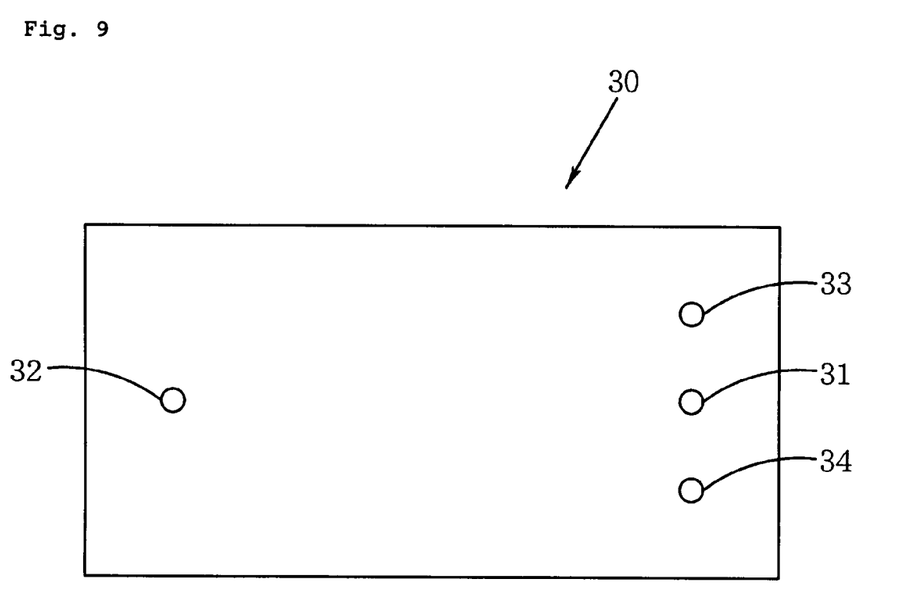
FIG. 9 is a view showing a shape of a connecting plate.
Figure 10:
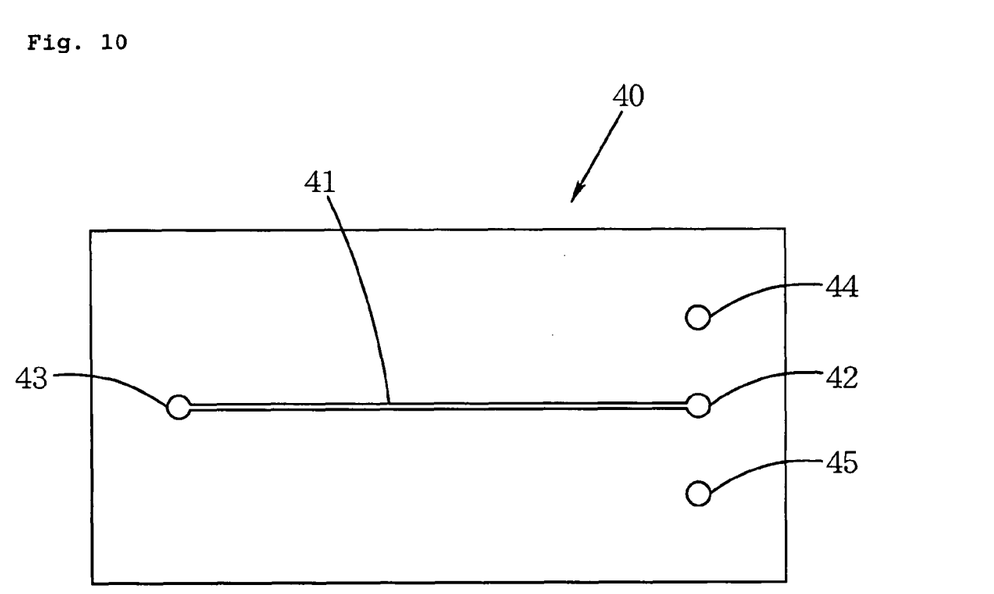
FIG. 10 is a view showing a shape of a reaction plate of a linear type.
Figure 11:
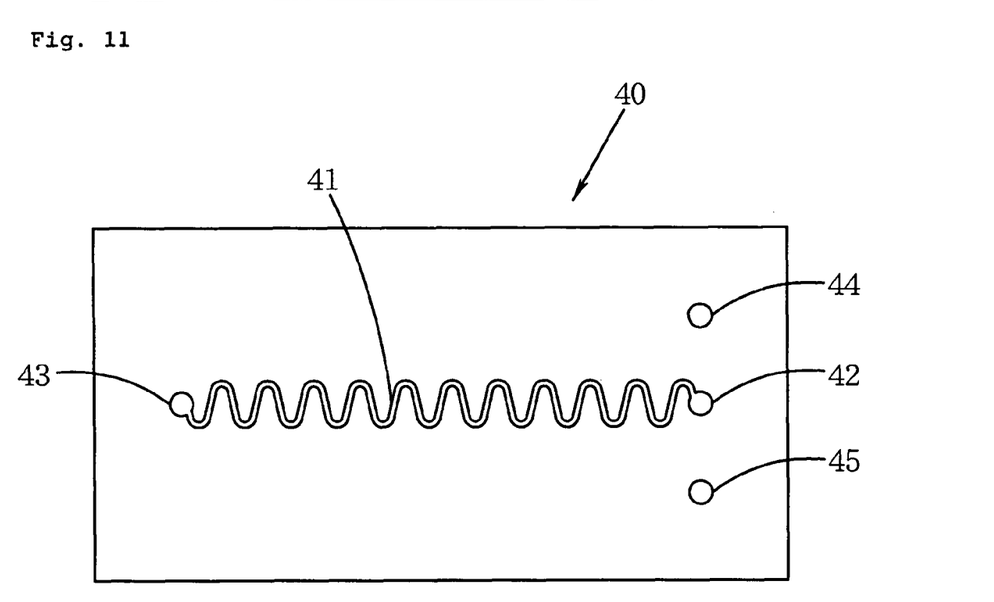
FIG. 11 is a view showing a shape of a reaction plate of a little wave type.
Figure 12:
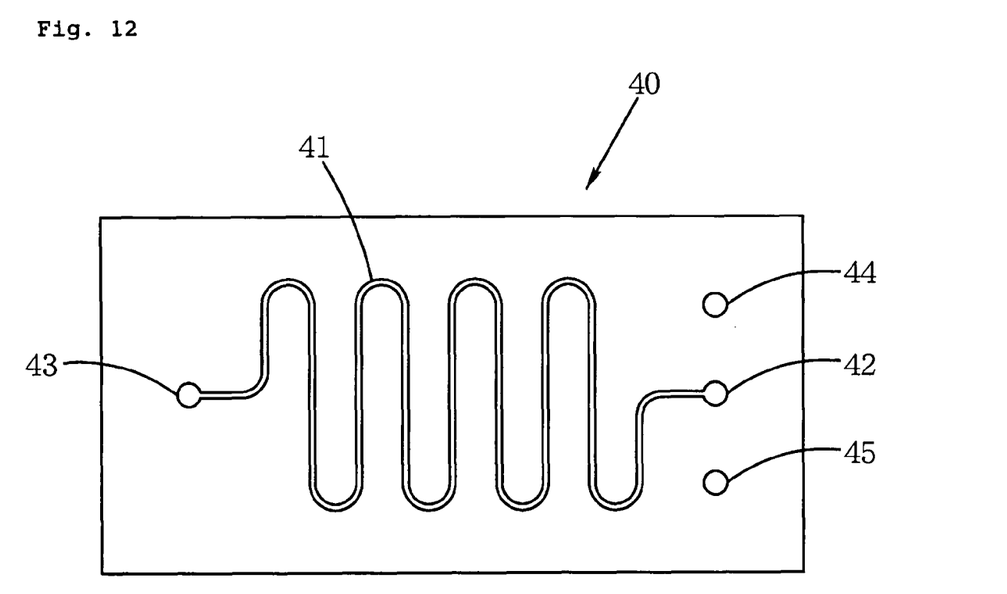
FIG. 12 is a view showing a shape of a reaction plate of a large wave type.
Figure 13:
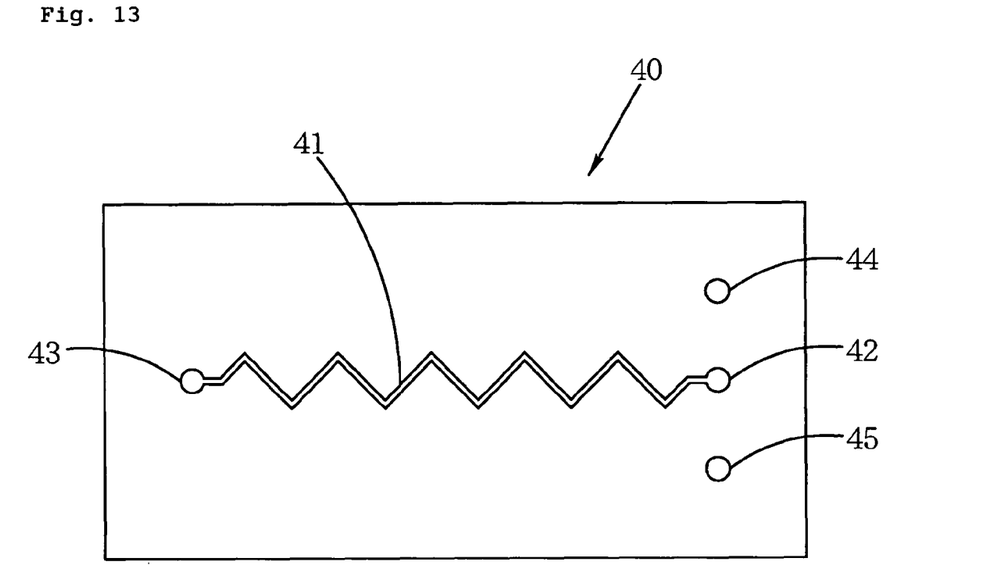
FIG. 13 is a view showing a shape of a reaction plate of a serrate type.

The connecting plate 30 is a quartz glass plate having a length of 60 mm, a width of 30 mm and a thickness of 1 mm, and has the shape shown in FIG. 9. Through holes 31, 32, 33 and 34 having a diameter of 2 mm are provided. The through hole 31 is connected to the through hole 27 of the merging plate and a through hole 42 of the reaction plate 40 to constitute a part of the flow control section 80. Only one particle 82 constituted by a glass ball is placed inside the flow control section 80. The through holes 33 and 34 are provided for the liquid having been separated with the separating plate 60 flowing to the deriving ports 13 and 14. The through hole 32 is dead ended.

The reaction plate 40 is a stainless steel plate having a length of 60 mm, a width of 30 mm and a thickness of 0.5 mm and having a slit having a width of 0.5 mm formed therein, and the slit constitutes a reaction channel 41. Four kinds of reaction plates 40 having various slit shapes including "linear type (FIG. 10)", "little wave type (FIG. 11)", "large wave type (FIG. 12)" and "serrate type (FIG. 13)" are subjected to the test. A through hole 42 having a diameter of 2 mm is provided at an end part on the upstream side of the reaction channel 41 and connected to the through hole 31 of the connecting plate 30 to constitute a part of the flow control section 80. A through hole 43 having a diameter of 2 mm is provided on an end part on the downstream side of the reaction channel 41 and connected to a through hole 52 of the connecting plate 50. Through holes 44 and 45 are provided for the liquid having been separated with the separating plate 60 to flow to the deriving ports 13 and 14.

Figure 14:
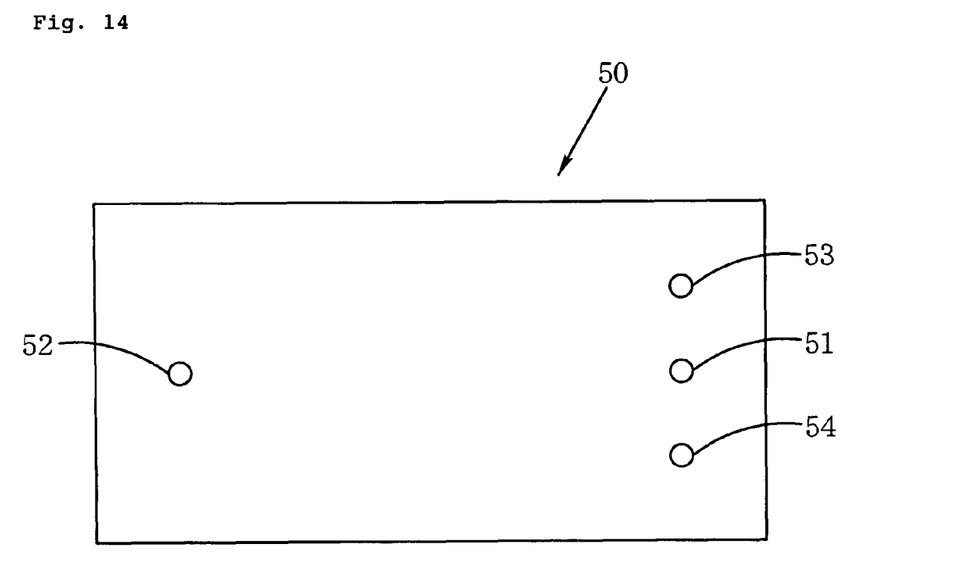
FIG. 14 is a view showing a shape of a connecting plate.

The connecting plate 50 is a quartz glass plate having a length of 60 mm, a width of 30 mm and a thickness of 1 mm, and has the shape shown in FIG. 14. It has the same shape as the connecting plate 30, and through holes 51, 52, 53 and 54 having a diameter of 2 mm are provided. The through hole 52 is connected to a through hole 65 of the separating plate 60. The through holes 53 and 54 are provided for the liquid having been separated with the separating plate 60 to flow to the deriving ports 13 and 14. The through hole 51 is dead ended.

Figure 15:
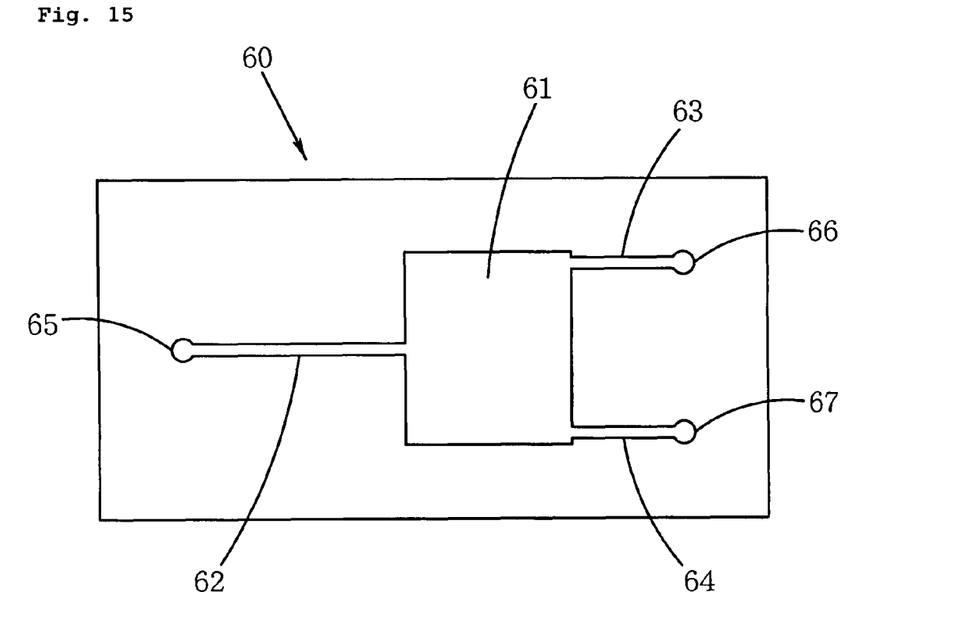
FIG. 15 is a view showing a shape of a separating plate.

The separating plate 60 is a stainless steel plate having a length of 60 mm, a width of 30 mm and a thickness of 0.5 mm and having a square separating section 61 punched out therein, and has the shape shown in FIG. 15. A channel 62 constituted by a slit having a width of 1 mm is formed on the upstream side of the separating section 61, and a through hole 65 having a diameter of 2 mm is formed at an end part on the upstream side thereof. The through hole 65 is connected to the through hole of the connecting plate 50. Channels 63 and 64 constituted by slits having a width of 1 mm are formed at two locations on upside and downside on the downstream side of the separating section 61, and through holes 66 and 67 having a diameter of 2 mm are formed at an end part on the downstream side thereof. The through hole 66 is connected to the deriving port 13, and the through hole 67 is connected to the deriving port 14. The separating section 61 has a volume of 0.113 mL. The backside plate 70 is a quartz glass plate having a length of 60 mm, a width of 30 mm and a thickness 3 mm.

The following chemical reaction was carried out by using the aforementioned microreactor. As an oily phase, a hexane solution having dissolved therein 0.002 mol/L of bis(di(2-ethylhexyl)phosphate) copper(II) as a complex containing copper ions was used. As an aqueous phase, an aqueous solution having dissolved therein 1.0 mol/L of hydrochloric acid was used. Copper(II) chloride was formed through contact of the oily phase and the aqueous phase, and dissolved in the aqueous phase. The reaction formula is shown below. Accordingly, copper(II) ions are extracted from the oily phase to the aqueous phase with progress of the reaction. The flow state in the reaction channel 41 can be observed through the separating section 61.

[Chemical 1]

The oily phase and the aqueous phase were fed from the introduction port 11 and the introduction port 12, respectively, by using a microsyringe pump. After passing through the merging plate 20, the reaction plate 40 and the separating plate 60 in this order, the oily phase and the aqueous phase were recovered from the deriving port 13 and the deriving port 14, respectively, and were measured for copper ion concentration with an atomic absorption spectrophotometer. The extraction percentage E (%) was obtained according to the following expression (1).

$$E = (Ca \cdot Va/(Ca \cdot Va + Co \cdot Vo)) \times 100 (\%) \quad (1)$$

Ca: Copper(II) ion concentration (mol/L) of aqueous phase
Co: Copper(II) ion concentration (mol/L) of oily phase
Va: Volume (L) of recovered aqueous phase
Vo: Volume (L) of recovered oily phase The volume of the channel where the two kinds of liquids are in contact with each other is the total volume of from the merging section 23 to the separating section 61. The volume (Vr) of the channel varies depending on the kind of the reaction plate 40, and is 0.168 mL for the linear type, 0.174 mL for the little wave type, 0.199 mL for the large wave type, and 0.172 for the serrate type. The contact time τ (sec) within the microreactor was obtained according to the following expression (2).

$$\tau = t \cdot Vr/(Va+Vo) \text{(sec)} \quad (2)$$

t: Collecting time (sec) of recovered liquid
Vr: Volume (L) of channel of microreactor
Va: Volume (L) of recovered aqueous phase
Vo: Volume (L) of recovered oily phase Example 1

The flow state in the reaction channel 41 was observed in the case where the glass ball was introduced and the case where it was not introduced, by using four kinds of reaction plates 40, i.e., the linear type, the little wave type, the large wave type and the serrate type, with variation in flow rate. The volume ratio of the oily phase and the aqueous phase upon introduction was fixed to 1/1, and the glass ball having a diameter of 1.21 mm was used. In all the cases, the oily phase and the aqueous phase were favorably separated and recovered. The results are collectively shown in Table 1. The flow rates shown in Table 1 are for one of the oily phase or the aqueous phase.

TABLE 1

| Flow rate (mL/min) | Particle not introduced | Particle introduced |
|---|---|---|
| Linear type | | |
| 0.126 | alternating flow L = 46 mm | parallel two-phase flow |
| 0.063 | alternating flow L = 56 mm | parallel two-phase flow |
| 0.032 | alternating flow L = 56 mm | parallel two-phase flow |
| Little wave type | | |
| 0.130 | alternating flow L = 22 to 30 mm | alternating flow L = 6 mm |
| 0.065 | alternating flow L = 30 mm | alternating flow L = 6 mm |
| 0.033 | alternating flow L = 56 mm | alternating flow L = 6 mm |
| Large wave type | | |
| 0.149 | parallel two-phase flow | parallel two-phase flow |
| 0.075 | alternating flow L = 76 mm | parallel two-phase flow |
| 0.037 | alternating flow L = 76 mm | parallel two-phase flow |
| Serrate type | | |
| 0.126 | alternating flow L = 12 to 24 mm | parallel two-phase flow alternating flow L = 6 mm |
| 0.063 | alternating flow L = 66 mm | alternating flow L = 6 mm |
| 0.032 | alternating flow L = 76 mm | alternating flow L = 6 to 16 mm |

As shown in Table 1, in the case where the reaction plate of the linear type or the large wave type was used, and the glass ball was not introduced, an alternating flow having a long pitch was mainly observed, but there were some cases where a parallel two-phase flow was observed, to provide insufficient reproducibility. It was understood on the other hand that a parallel two-phase flow was formed with good reproducibility over a wide range of flow rate by introducing the glass ball. In the case where the reaction plate 40 of the little wave type or the serrate type was used, and the glass ball was not introduced, an alternating flow having a long pitch was mainly observed, but there were some cases where a parallel two-phase flow was observed, to provide insufficient reproducibility. It was understood on the other hand that an alternating flow having a short pitch of 6 mm was formed with good reproducibility over a wide range of flow rate by introducing the glass ball. The value of 6 mm corresponds to the one cycle length of the sine wave in the little wave type or the length of the linear part from one bend section to another bend section in the serrate type. Accordingly, it is expected that the periodic bending contributes to the formation of a stable alternating flow having a short pitch.

Example 2

In the case of the microreactor used in Example 1, it is difficult to observe directly the movement of the particle 82 in the flow control section 80 since it is shielded with the separating plate 60. Accordingly, simultaneously with introduction of the particle 82 to the flow control section 80, the same particle was introduced to the through hole 52 of the connecting plate 50 for carrying out the test. The particle in the through hole 52 can be observed through the backside plate 70 made of glass. Upon observing the movement of the particle in the through hole 52 during an alternating flow was formed, the position of the particle where the oily phase flowed in the through hole 52 was different from the position of the particle where the aqueous phase flowed in the through hole 52, and as a result, oscillation of the particle corresponding to the pitch of the alternating flow formed was observed. It is understood that the position of the particle varies depending on the density, viscosity, affinity to the liquid and the like, and it is expected that the similar phenomenon occurs in the particle 82 in the flow control section 80.

Example 3

In the case using a microreactor having the same constitution as in Example 1 using the reaction plate 40 of the little wave type, when the microreactor was totally fallen sideway, a regular alternating flow having a short pitch could not be formed to provide the same result as in the case of carrying out the test without the glass ball introduced. Accordingly, it is expected that the particle 82 is placed on the curvature of the lower surface 83 of the channel 81 in the flow control section 80 as shown in FIG. 3 by making the microreactor in the direction shown in FIG. 1, whereby oscillation is facilitated through the balance between gravity and flow. It is also considered that the bending in the vertical direction of the reaction channel 41 contributes to the formation of an alternating flow.

Furthermore, in the case using the reaction plate 40 of the little wave type, the particle 82 was placed on the side near the merging plate 20 in the channel 81 of the flow control section 80 of the microreactor having been fallen sideway, and the test was carried out after returning the microreactor in the direction shown in FIG. 1. Then, a regular alternating flow having a short pitch could not be formed to provide the same result as in the case of carrying out the test without the glass ball introduced in Example 1. When the test was then carried out again after moving the glass ball to the position near the reaction plate 40 by aspirating through the deriving holes 13 and 14, an alternating flow having a regular pitch was formed as similar to Example 1. It is understood that in the channel 81 of the flow control section 80, the particle 82 is preferably disposed at a position near the reaction channel 41 rather than channel 24.

Example 4

Figure 16:
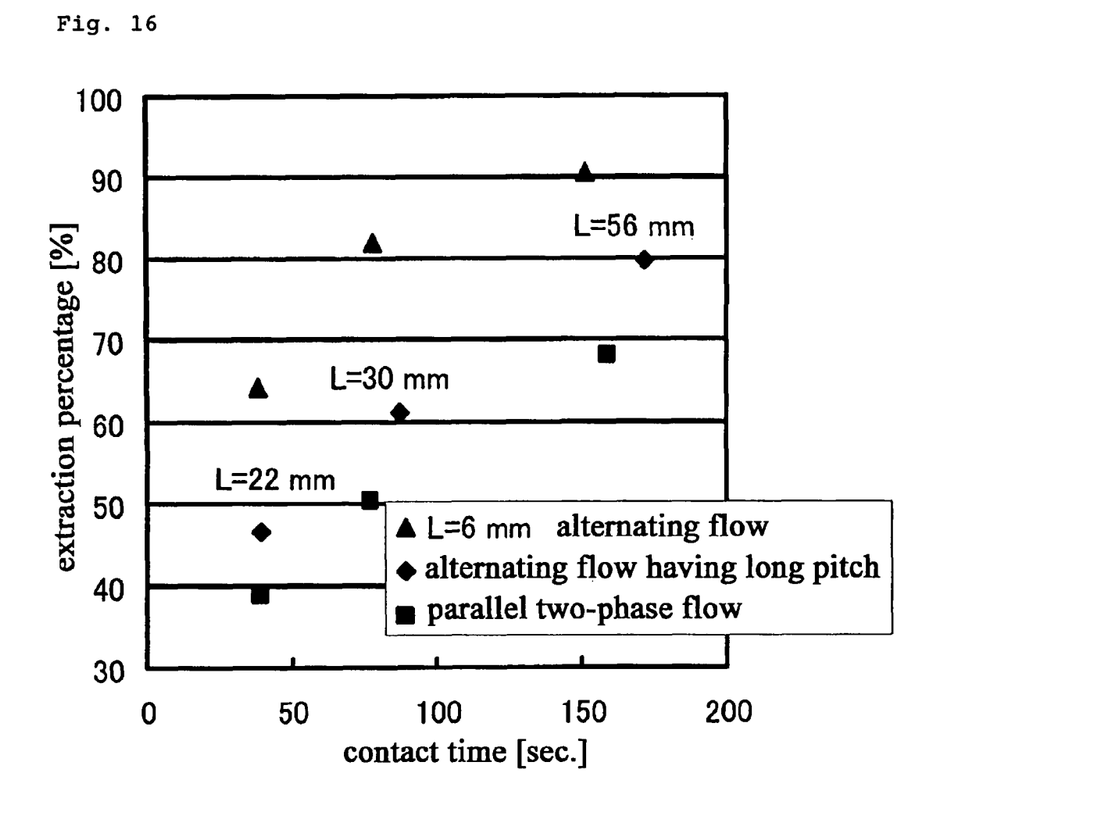
FIG. 16 is a graph showing relationship between a contact time τ (sec) and an extraction percentage E (%).

FIG. 16 is a graph showing relationship between the contact time τ (sec) and the extraction percentage E (%) in the case where the reaction plate 40 of the little wave type is used. In the case where the glass ball was not introduced, there were a case where a parallel two-phase flow was formed and a case where an alternating flow having a long pitch was formed with poor reproducibility in flow state, and therefore, data was obtained in both cases. Data where an alternating flow having a short pitch of about 6 mm was formed was obtained from the test where the glass ball was introduced. The test method was the same as in Example 1.

As understood from FIG. 16, the extraction percentage (E) with a fixed contact time (τ) was the highest for an alternating flow with a short pitch, the next for an alternating flow with a long pitch, and the lowest for a parallel two-phase flow. It is unexpected that a higher extraction percentage than that for a parallel two-phase flow is obtained even though the pitch is as long as from 22 to 56 mm. It is apparent from the fact that formation of an alternating flow, particularly an alternating flow having a short pitch, is advantageous for the case where chemical reaction or extraction is carried out.

Example 5

The same test as in Example 1 was carried out in the case where the reaction plate 40 of the little wave type was used except that the dimension of the glass ball was changed. Glass balls having diameters of 0.95 mm, 1.07 mm, 1.21 mm and 1.62 mm were used. The channel 81 of the flow control section 80 had an inner diameter of 2.0 mm, and thus all the glass balls had a dimension capable of moving therein. The reaction channel 41 had a circle equivalent diameter of 0.56 mm, and thus the diameters of the glass balls were 1.68 times, 1.90 times, 2.14 time and 2.87 times the circle equivalent diameter, respectively. The flow states observed are collectively shown in Table 2. The flow rates shown in Table 2 are for one of the oily phase or the aqueous phase.

TABLE 2

| Flow rate (mL/min) | Flow state |
|---|---|
| Particle not introduced | |
| 0.033 | alternating flow L = 56 mm |
| 0.065 | alternating flow L = 30 mm |
| 0.13 | alternating flow L = 22 to 30 mm |
| 0.3 | interface not visible |
| Particle diameter: 0.95 mm | |
| 0.033 | alternating flow L = 48 mm |
| 0.065 | alternating flow L = 48 mm |
| 0.13 | parallel two-phase flow |
| Particle diameter: 1.07 mm | |
| 0.033 | alternating flow L = 6 mm |
| 0.065 | alternating flow L = 6 mm |
| 0.13 | alternating flow L = 6 mm |
| 0.2 | alternating flow L = 6 mm |
| 0.25 | parallel two-phase flow |
| Particle diameter: 1.21 mm | |
| 0.033 | alternating flow L = 6 mm |
| 0.065 | alternating flow L = 6 mm |
| 0.13 | alternating flow L = 6 mm |
| 0.2 | alternating flow L = 6 mm |
| 0.25 | parallel two-phase flow |
| Particle diameter: 1.62 mm | |
| 0.033 | alternating flow L = 6 to 12 mm |
| 0.065 | alternating flow L = 6 mm |
| 0.13 | parallel two-phase flow |

It was understood from the results in Table 2 that the dimension of the glass ball influenced the flow state. For example, it seems that the particle 82 having a dimension that reasonably masks the flow is preferably used for forming an alternating flow having a short pitch with good reproducibility.

Example 6

The same test as in Example 1 was carried out in the case where the reaction plate 40 of the little wave type was used except that the flow ratio of the aqueous phase and the oily phase was changed. The flow state was observed where the flow rate of the aqueous phase was fixed to 0.065 mL/min, and the flow rate of the oily phase was changed to 0.2 time, 0.5 time, 1 time, 2 times and 5 times that of the aqueous phase. The flow state was also observed where the flow rate of the oily phase was fixed to 0.065 mL/min, and the flow rate of the aqueous phase was changed to 0.2 time, 0.5 time, 1 time, 2 times and times that of the oily phase. The results are collectively shown in Table 3.

TABLE 3

| Particle not introduced | | Particle introduced | |
|---|---|---|---|
| Flow ratio (aqueous/oily) | Flow state | Flow ratio (aqueous/oily) | Flow state |
| Flow rate of aqueous phase fixed (0.065 mL/min) | | | |
| 1/0.2 | alternating flow L = 59 mm | 1/0.2 | alternating flow L = 15.5 mm |
| 1/0.5 | alternating flow L = 44 mm | 1/0.5 | alternating flow L = 7.5 mm |
| 1/1 | alternating flow L = 60 mm | 1/1 | alternating flow L = 6 mm |
| 1/2 | alternating flow L = 32 mm | 1/2 | alternating flow*[1] |
| 1/5 | interface not visible | 1/5 | alternating flow*[1] |
| Flow rate of oily phase fixed (0.065 mL/min) | | | |
| 5/1 | alternating flow L = 101 mm | 5/1 | parallel two-phase flow |
| 2/1 | alternating flow L = 68 mm | 2/1 | parallel two-phase flow alternating flow*[1] |
| 1/1 | alternating flow L = 60 mm | 1/1 | alternating flow L = 6 mm |
| 0.5/1 | alternating flow L = 63 mm | 0.5/1 | alternating flow L = 7 mm |
| 0.2/1 | alternating flow L = 107 mm | 0.2/1 | alternating flow L = 7.5 mm |

*[1]Measurement of the pitch (L) was difficult due to too large flow rates.

It was understood from the results in Table 3 that an alternating flow was liable to be formed when the flow ratio of the aqueous phase and the oily phase was close to 1/1. It was also understood that an alternating flow having a short pitch was formed over a relatively wide range of flow ratio in the case where a glass ball was introduced.

The invention claimed is:

1. A method of chemical reaction using a microreactor comprising a plurality of introduction channels for introducing liquids, a merging section for merging the plurality of introduction channels, and a reaction channel located on a downstream side of the merging section, wherein a flow control section is located on a downstream side of the merging section and an upstream side of the reaction channel, and the flow control section contains in a channel thereof only one movable particle having a spherical shape,
   the method comprising introducing a plurality of liquids that are incompatible with each other to the plurality of introduction channels, and
   forming an alternating flow of the plurality of liquids in the reaction channel in which chemical reaction proceeds by periodic oscillation of the particle.

2. The method of chemical reaction according to claim 1, wherein the introduction channels have a circle equivalent diameter of from 0.01 to 2 mm.

3. The method of chemical reaction according to claim 1, wherein a lower surface or an upper surface of the channel of the flow control section is curved.

4. The method of chemical reaction according to claim 1, wherein the particle is capable of being forcedly moved by applying a magnetic field or an electric field.

5. The method of chemical reaction according to claim 1, wherein the reaction channels have a circle equivalent diameter of from 0.01 to 2 mm.

6. The method of chemical reaction according to claim 1, wherein the channel of the flow control section has a cross sectional area that is larger than a cross sectional area of the reaction channel, and the particle has such a dimension that the particle is capable of moving in the channel of the flow control section but is not capable of entering in the reaction channel.

7. The method of chemical reaction according to claim 1, wherein the reaction channel is bent periodically.

8. The method of chemical reaction according to claim 1, wherein the reaction channel is bent in the vertical direction.

9. The method of chemical reaction according to claim 1, wherein the microreactor further comprises a separating section having a larger cross sectional area on a downstream side of the reaction channel, and the separating section has an upper part and a lower part connected to channels for deriving the liquids after separating.

10. The method of chemical reaction according to claim 1, wherein the microreactor further comprises a separating section having a larger cross sectional area on a downstream side of the reaction channel, the separating section has an upper part and a lower part connected to channels for deriving the liquids after separating, a liquid having a low density is derived from the channel of the upper part, and a liquid having a high density is derived from the channel of the lower part.

11. A method of extraction using a microreactor comprising a plurality of introduction channels for introducing liquids, a merging section for merging the plurality of introduction channels, and a reaction channel located on a downstream side of the merging section, wherein a flow control section is located on a downstream side of the merging section and an upstream side of the reaction channel, and the flow control section contains in a channel thereof only one movable particle having a spherical shape,
   the method comprising introducing a plurality of liquids that are incompatible with each other to the plurality of introduction channels, and
   forming an alternating flow of the plurality of liquids in the reaction channel in which extraction proceeds by periodic oscillation of the particle.

12. The method of extraction according to claim 11, wherein the introduction channels have a circle equivalent diameter of from 0.01 to 2 mm.

13. The method of extraction according to claim 11, wherein a lower surface or an upper surface of the channel of the flow control section is curved.

14. The method of extraction according to claim 11, wherein the particle is capable of being forcedly moved by applying a magnetic field or an electric field.

15. The method of extraction according to claim 11, wherein the reaction channels have a circle equivalent diameter of from 0.01 to 2 mm.

16. The method of extraction according to claim 11, wherein the channel of the flow control section has a cross sectional area that is larger than a cross sectional area of the reaction channel, and the particle has such a dimension that the particle is capable of moving in the channel of the flow control section but is not capable of entering in the reaction channel.

17. The method of extraction according to claim 11, wherein the reaction channel is bent periodically.

18. The method of extraction according to claim 11, wherein the reaction channel is bent in the vertical direction.

19. The method of extraction according to claim 11, wherein the microreactor further comprises a separating section having a larger cross sectional area on a downstream side of the reaction channel, and the separating section has an upper part and a lower part connected to channels for deriving the liquids after separating.

20. The method of extraction according to claim 11, wherein the microreactor further comprises a separating section having a larger cross sectional area on a downstream side of the reaction channel, the separating section has an upper part and a lower part connected to channels for deriving the liquids after separating, a liquid having a low density is derived from the channel of the upper part, and a liquid having a high density is derived from the channel of the lower part.

* * * * *